United States Patent
Bodine

(10) Patent No.: US 8,657,139 B1
(45) Date of Patent: Feb. 25, 2014

(54) SYSTEM FOR DELIVERING DEODORIZER AND REPELLENT FOR A CONTAINER

(71) Applicant: Julia Ann Bodine, Seaford, NY (US)

(72) Inventor: Julia Ann Bodine, Seaford, NY (US)

(*) Notice: Subject to any disclaimer, the term of this patent is extended or adjusted under 35 U.S.C. 154(b) by 0 days.

(21) Appl. No.: 13/660,052

(22) Filed: Oct. 25, 2012

(51) Int. Cl.
*B65D 25/00* (2006.01)

(52) U.S. Cl.
USPC ........ 220/87.1; 220/730; 220/908; 220/908.2

(58) Field of Classification Search
USPC .............................. 220/87.1, 730, 908, 908.2
See application file for complete search history.

(56) References Cited

U.S. PATENT DOCUMENTS

| | | | |
|---|---|---|---|
| 1,637,656 A | | 8/1927 | Radcliffe |
| 1,656,015 A | * | 1/1928 | Radcliffe ..................... 220/87.1 |
| 1,719,185 A | | 7/1929 | Lowy |
| 2,147,139 A | | 2/1939 | Bigman et al. |
| 2,721,099 A | * | 10/1955 | Rupp ............................. 239/57 |
| 2,802,590 A | * | 8/1957 | Tupper ......................... 220/522 |
| 3,098,703 A | | 7/1963 | Snyder et al. |
| 3,102,661 A | | 9/1963 | Lundquist |
| 3,214,065 A | | 10/1965 | Thornton |
| 3,346,140 A | * | 10/1967 | Mele ........................... 220/87.1 |
| 4,202,472 A | * | 5/1980 | Lin ............................... 222/187 |
| 4,427,110 A | | 1/1984 | Shaw, Jr. |
| 5,174,462 A | | 12/1992 | Hames |
| 5,799,909 A | * | 9/1998 | Ziegler ......................... 248/101 |
| 5,862,932 A | * | 1/1999 | Walsh et al. ..................... 220/8 |
| 5,988,520 A | * | 11/1999 | Bitner .............................. 239/6 |
| 7,878,359 B1 | * | 2/2011 | Ko .............................. 220/87.2 |
| 2006/0081632 A1 | * | 4/2006 | Shieh .......................... 220/87.1 |
| 2007/0039965 A1 | | 2/2007 | Todd |

FOREIGN PATENT DOCUMENTS

JP          2005126167          5/2005

* cited by examiner

*Primary Examiner* — Anthony Stashick
*Assistant Examiner* — Madison L Poos
(74) *Attorney, Agent, or Firm* — John F. Vodopia Esq

(57) ABSTRACT

A system for delivering deodorizer or repellent or both is intended for use with a household or commercial container including a cover. The system includes a first receptacle formed as a first housing shell surrounding a volume for holding a repellent or deodorizer, where openings allow part of the repellent or deodorizer to escape into the environment when the first receptacle is positioned on the outer cover surface and the cover is positioned on the container. A second receptacle formed as a second housing shell surrounding an inner volume for holding a repellent or deodorizer, where openings allow part of the repellent or deodorizer to escape into the inner container environment when the second receptacle is positioned on the inner cover surface and the cover is positioned on the container. A connector detachably connects the receptacles.

17 Claims, 9 Drawing Sheets

SYSTEM FOR DELIVERING DEODORIZER AND REPELLENT FOR A CONTAINER

BACKGROUND OF THE INVENTION

The present invention relates to a system for delivering deodorizer and/or repellent for a container such as outdoor or indoor trash containers, laundry containers, diaper containers, etc.

Garbage containers, dumpsters, dirty laundry containers, diaper pails, etc., whether indoor or out, are known to exude some very foul odors and gases. But not only are the odors and/or gases offensive, they attract vermin such as small rodents and insects as well as larger animals such as racoons or even bears.

Various attempts to overcome problems associated with malodorous containers, e.g., garbage or trash, laundry, diaper, etc. are known.

For example, U.S. Pat. No. 1,637,656 ("the '656 patent") discloses a cover for garbage cans having a cover in which a depression formed as a disinfectant receiving receptacle. That is, the invention provides a removable cover C for a garbage can, the cover C having depending flanges 10 configured to slip over the sides of the can G. At about the center of the cover C is formed a depression with a substantially horizontal bottom 11 and approximately vertical side walls 12 forming a perforated receptacle adapted to receive a disinfectant or the like, the perforations shown at 13 and formed in the side walls a short distance from the bottom 10. The receptacle can be formed by stamping the cover C downwardly (integral), or attaching. The side walls 12 may include threads 14, where a closure 15 is provided with depending flanges 16 adapted to telescope within the side walls. A handle 17 is rigidly secured to the closures 15.

While the '656 patent does provide a cover C that is configured to deliver a disinfectant to an inner portion of the garbage can G, via depression formed as a perforated receptacle, the amount of disinfectant delivered does not appear to be controllable by the receptacle structure. For that matter, the receptacle does not provide a means for delivering disinfectant outside the garbage can G, or for ready attachment to a cover in a garbage can that does not have a portion cut-out.

Also known is pending US Patent Appln. Ser. no. 2007/0039965 ("the '965 application"), which discloses a compound lid for masking/overcoming obnoxious odors in garbage containers, dirty laundry containers, diaper pails, etc., by releasing a pleasant fragrance into the air after each container use. In more detail, a gel air freshener releases fragrance from the lid's vent opening in the air and in one embodiment, a mist air freshener releases fragrance from a nozzle in the air. Hence, the inventive lid allows two separate and distinct scented media to interface with the air and thereby disperse alternately or simultaneously (creating a stronger scent) depending on the operators preference, one being the gel air freshener and the other being the mist air freshener. The lid 10 is dome shaped and includes a solid layer of molded plastic 12 surrounding the bottom walls 6. Layer 12 keeps trash, laundry, diapers, etc. from coming in contact with the gel air fragrance 38 and mist air fragrance 34.

The '965 application, however, only delivers fragrance outside the container, and like the '656 patent, appears intended to be used to replace an original container lid. That is, the '965 application does not appear to teach or suggest that a lid that has previously been purchased for use with a container might be modified to operate as does dome-shaped lid 10.

For that matter, and again, like the lid found in the '656 patent, dome-shaped lid 10, does not teach or suggest delivering one substance to the outside and one substance inside.

SUMMARY OF THE INVENTION

The present invention provides a system for delivering deodorizer and/or repellent for a container such as an outdoor trash container that is designed to overcome the shortcomings of the prior art.

In an embodiment, the invention provides a system for delivering deodorizer or repellent or both is intended for use with a household or commercial container including a cover. The system includes a first receptacle formed as a first housing shell surrounding a volume for holding a repellent or deodorizer, where openings allow part of the repellent or deodorizer to escape into the environment when the first receptacle is positioned on the outer cover surface and the cover is positioned on the container. A second receptacle formed as a second housing shell surrounding an inner volume for holding a repellent or deodorizer, where openings allow part of the repellent or deodorizer to escape into the inner container environment when the second receptacle is positioned on the inner cover surface and the cover is positioned on the container. A connector detachably connects the receptacles.

During intended use, an end of the connector is passed through a through-hole in a container cover having substantially planar upper and lower surfaces in order to interconnect the first receptacle to the second receptacle such that the first receptacle is positioned upon and above the upper surface of the container cover and the second receptacle is positioned upon and below the lower surface of the cover

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

The following is a detailed description of example embodiments of the invention depicted in the accompanying drawings. The example embodiments are in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
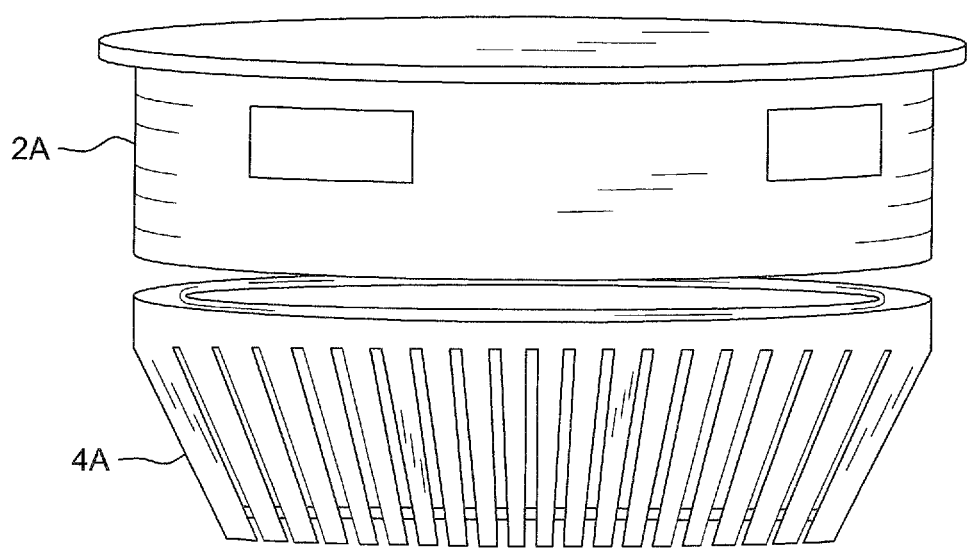
FIG. 1 is a side perspective view of one embodiment a system for delivering deodorizer and/or repellent for a container.

FIG. 1 provides an exploded side perspective view of one embodiment of a system for delivering deodorizer or repellent for a container. Preferably, the inventive system is configured to cooperate with a container that facilitates delivery of both a deodorizer and a repellent, as in the exemplary figures. The system as shown comprises upper 2A and lower 4A substantially cylindrical housings that are interconnected by a connector 6 (not shown in FIG. 1). The upper cylindrical housing 2A forms a receptacle for maintaining a supply of deodorizer and/or repellent and includes openings or through-holes 18 to allow communication of same when the system is mounted or otherwise connected to a lid or cover 8 of a container (not shown in FIG. 1).

The lower cylindrical housing 4A forms another receptacle for maintaining a supply of deodorizer or repellent or both and includes openings or through-holes 28 to allow communication of same when the system is mounted or otherwise connected to a lid or cover of a container (not shown in FIG. 1). The upper cylindrical housing 2A or receptacle preferably contains a repellent for delivery outside the container where the lower cylindrical housing 4A or receptacle preferably contains a deodorizer for delivery inside the container. Please note that the terms receptacle and housing are used interchangeably herein, as the housing forms a receptacle with an inner volume for containing repellent and/or deodorizer.

The repellent is chosen by the user to repel insects and smaller animals such as rodents or squirrels or larger animals such as racoons, cats, dogs and even bears. For example, repellents may include without limitation peppermint oils, organic urine pellets, capsaicin, chilli pepper extracts and materials, piperine, mint, ammonia, cinnamon, chlorine, frankincense and myrrh, oil of black pepper and various products available on the market known for repelling insects and animals.

The deodorizer is chosen by the user to deodorize the inner volume of the container, and the gases and air that will escape upon removal of a container lid from a container. For example, deodorizers may include without limitation carbon chips, carbon granules, carbon sticks, mesh bags comprising carbon, activated carbon, materials that emit botanical fragrances, citrus fragrances, woodsy fragrances, floral fragrances, fruity fragrances, etc.

For that matter, while the upper and lower housings are preferably plastic, or polyvinyl, they are not limited thereto but may be formed with any material that may be extruded or made by injection molding and which can withstand any corrosive effects of the repellent and/or deodorizer and/or environmental conditions. For example, the first and second receptacle parts also may be formed of HDPE, polypropylene, hardened rubber, metal, recycled materials, or a combination of these materials.

Figure 2:
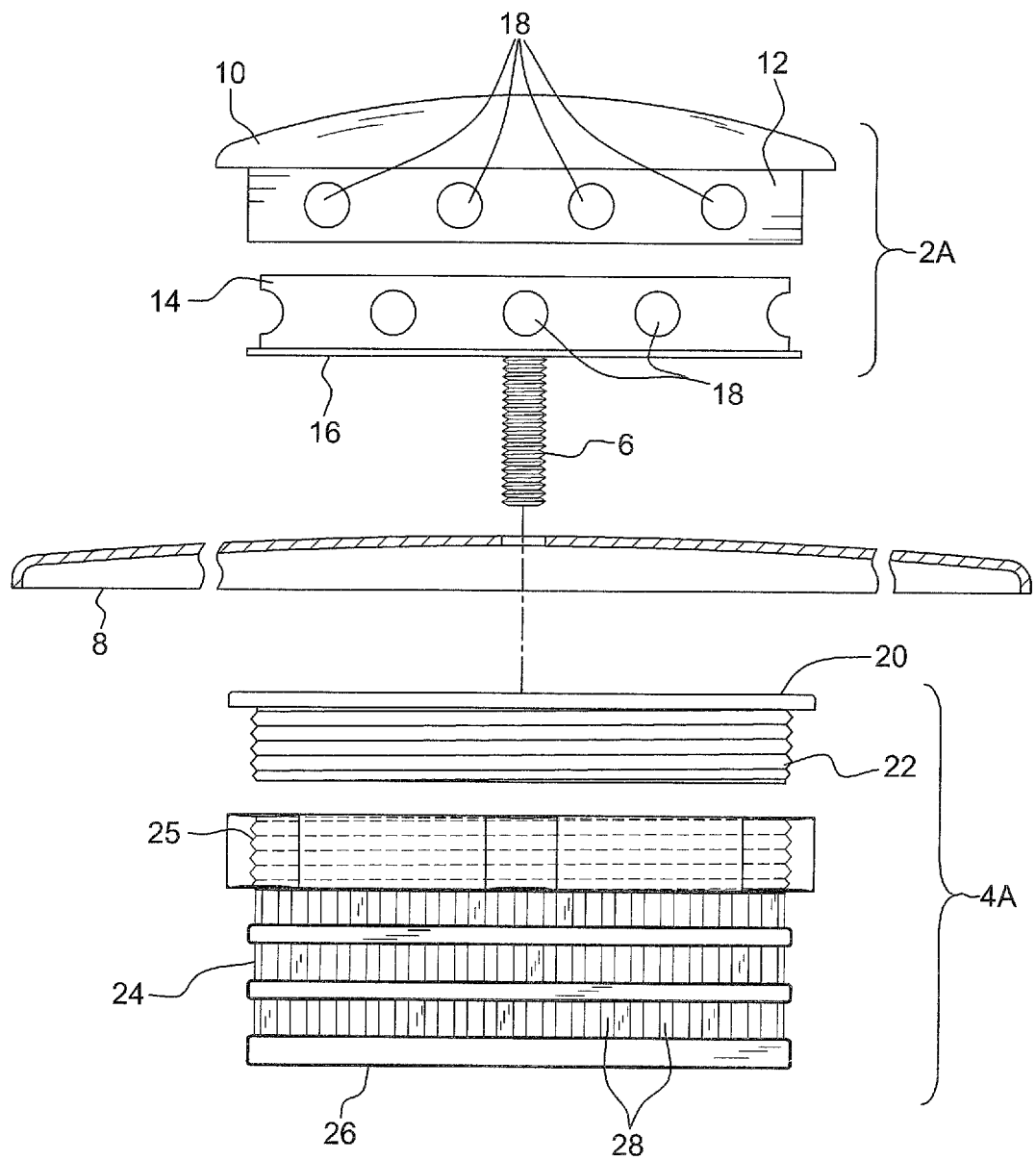
FIG. 2 is an exploded side view of another embodiment a system for delivering deodorizer and/or repellent for a container, including a container lid to which the system is affixable.

FIG. 2 is an exploded side view of another embodiment a system for delivering deodorizer and/or repellent for a container, including a container lid to which the system is affixable. The system as shown comprises upper 2A and lower 4A substantially cylindrical housings that are interconnected by a connector 6 through an opening in a lid or cover 8.

Figure 3A:
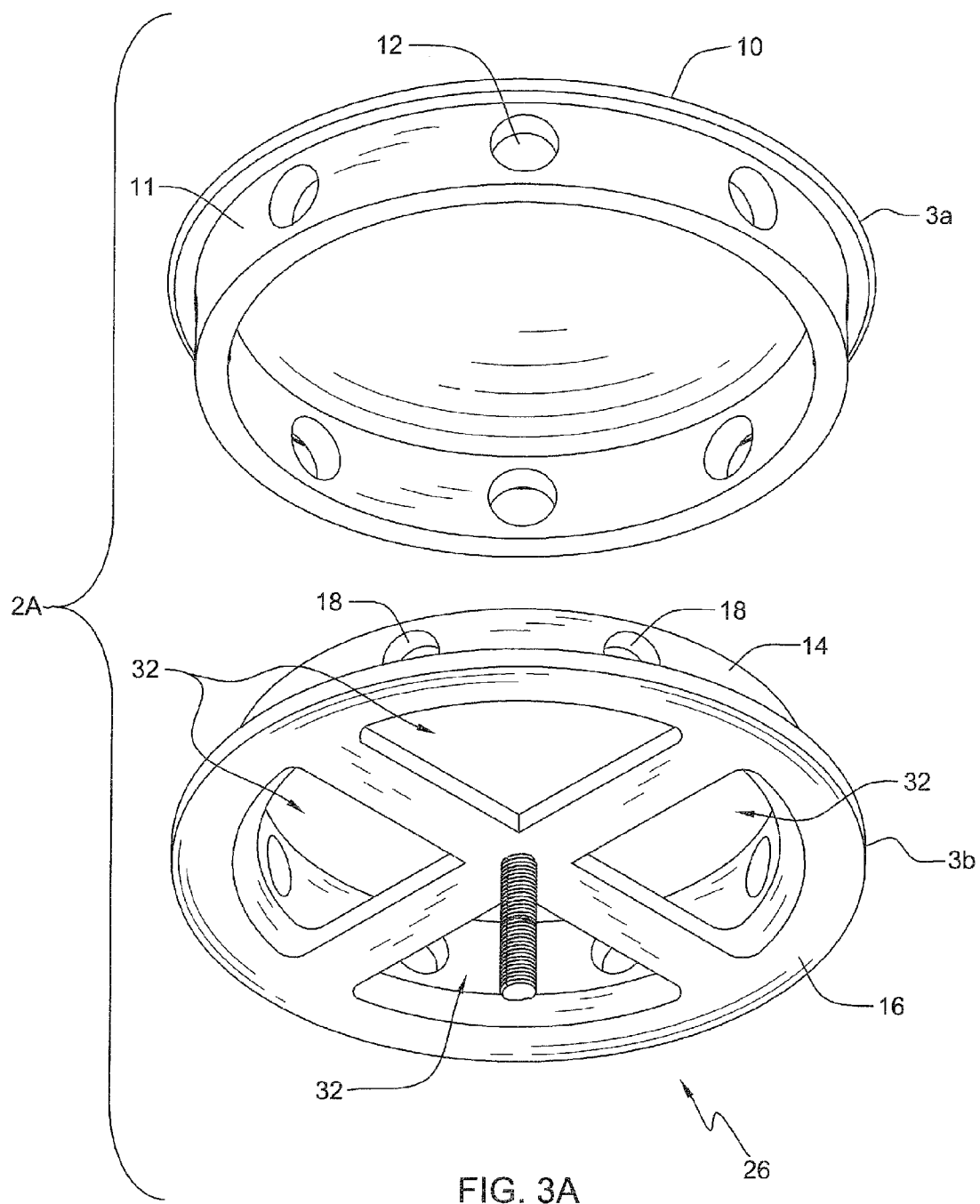
FIG. 3A presents an exploded side perspective view of an upper housing 2A for use in the system.

The upper housing 2A is comprised of two pieces, i.e., upper and lower sections 3a, 3b. The upper section 3a of upper housing 2A comprises a substantially arcuate upper part 10 or top from which depends or extends a flange-like portion 11. The upper section 3a also comprises a substantially cylindrical portion 12 that extends down from and uppermost part of the underside of the arcuate upper part or top 10, as shown. The lower section 3b of upper housing 2A comprises a substantially cylindrical portion 14 with a substantially flat base or surface 16. The cylindrical portion 14 of the lower section is open at its end opposite the flat base 16 and the cylindrical portion 12 of the upper section 3a is open at its end opposite the arcuate upper part 10 (see FIG. 3A).

A diameter of the substantially flat base or surface 16 of the lower section 3b is slightly larger than a diameter of the cylindrical portion 14 of the upper section, allowing for the lower section to slide over the upper section (i.e., the cylindrical portion 14) and form a cavity or receptacle to hold the repellent and/or deodorizer, preferably in a friction fit.

Alternatively, the diameter of the substantially flat base or surface 16 of the lower section is slightly less than a diameter of the cylindrical portion 14 of the upper section 3a, allowing for the upper section to slide over the lower section and form the cavity. For that matter, the embodiment shown is intended for exemplary purposes only. As such, the upper and lower sections of the upper housing (and the lower housing; see below) may be connected by any means known to the skilled artisan to form a receptacle or cavity capable of holding a deodorizer or a repellent or both.

For residential or household applications, the depth of the assembled upper housing or receptacle 2A is ¾ to 2 inches, but preferably 1 inch. The depth of the assembled lower housing or receptacle 2B also is ¾ to 2 inches, but preferably 1 inch. The width of both the upper 2A and lower 2B housings/receptacle are 2½ to 4 inches, but preferably 3 inches. Please note, however, as described above, the dimensions will vary depending on whether the upper or lower sections of each upper and lower housings or receptacles are configured to accommodate the fit.

For commercial applications, the depth of the assembled upper housing or receptacle 2A is 2 to 5 inches, but preferably 3 inches. The depth of the assembled lower housing or receptacle 2B also is 2 to 5 inches, but preferably 2 inches. The width of both the upper 2A and lower 2B housings/receptacle are 3½ to 10 inches, but preferably 6 inches. Please note, however, as described above, the dimensions will vary depending on whether the upper or lower sections of each upper and lower Housing or receptacle is configured to accommodate the fit.

Through-holes 18 in one or both the substantially cylindrical portion 12 of the upper section 3a of upper housing 2A and the substantially cylindrical portion 14 of the lower section 3b of upper housing 2A are included to facilitate fluid communication from the inner cavity or receptacle. That is, the cylindrical portions 12, 14 are rotated about an axial center of both the upper and lower sections (which axial centers are coaxial), to align the through-holes 18 in varying degree and affect an amount or size of an opening from the inner receptacle volume to the outside.

Alternatively, the upper receptacle may comprise an upper housing 2B configured to deliver a repellent or deodorizer via a set of openings that may be covered or exposed by sliding from a top surface. In more detail, upper housing 2B comprises three sections 3c, 3d and 3e. Section 3c is the cover section, which includes a handle part 7a in the axial center of the section from which radially extending slots 9. Section 3c is integral with or otherwise attached to a section 3d that includes openings 18 arranged in a line extending radially outward from an inner detent 7b at the axial center. The detent 7b slidingly cooperates with an opening in the handle 7a of section 3c, allowing section 3c to turn about the axial center of section 3*d* in order to align the slots 9 with the openings 18, or cause the openings 18 to be covered.

Sections 3*c* and 3*d* include a sliding mechanism on their respective outer radial surfaces that effects the attachment while allowing section 3*c* to slide axially. The attached sections 3*c* and 3*d* cooperate with section 3*e* in a way that is similar to the way section 3*a* cooperates and attached with section 3*b* (of upper housing 2A). For that matter, the opening in the outer side surface of section 3*e* are optional. In section 3*e*, a hole into which a connector 6 is inserted is identified with element identifier 7*c*.

Figure 3B:
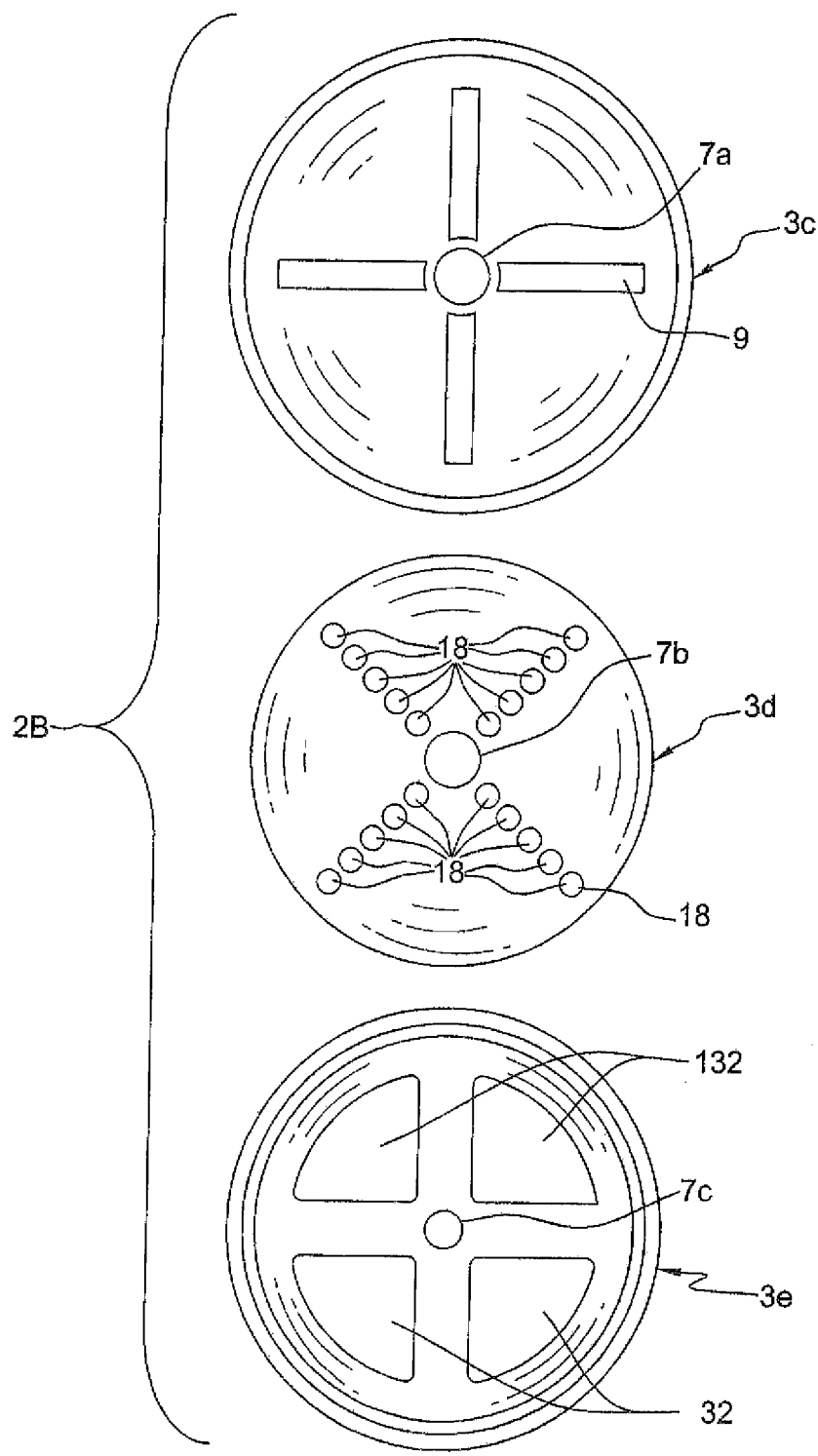
FIG. 3B presents a view of the elements comprising an alternative upper housing 2B for use in the system.
Figure 3C:
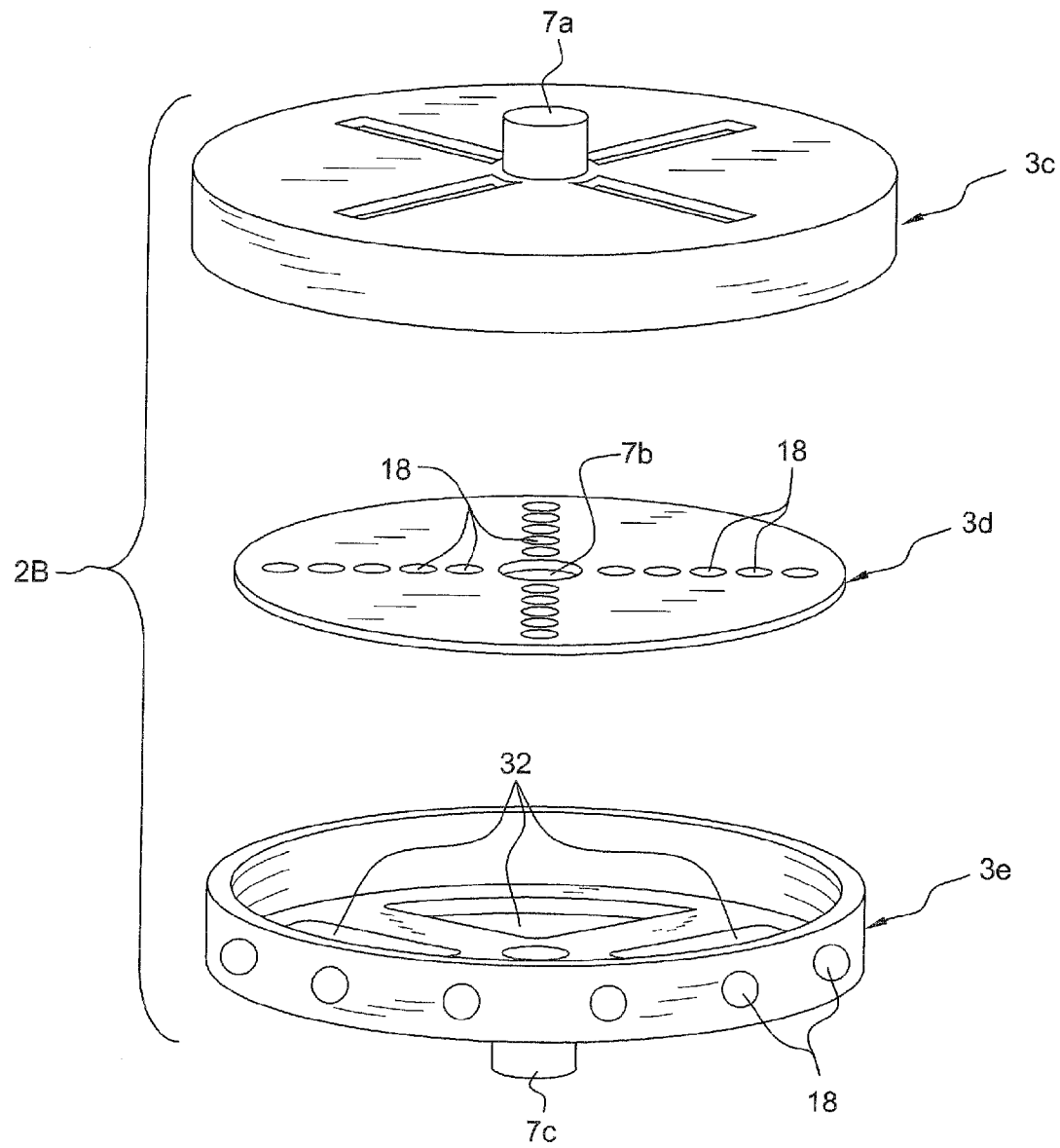
FIG. 3C presents an exploded side perspective of the alternative upper housing 2B depicted in FIG. 3B.
Figure 5:
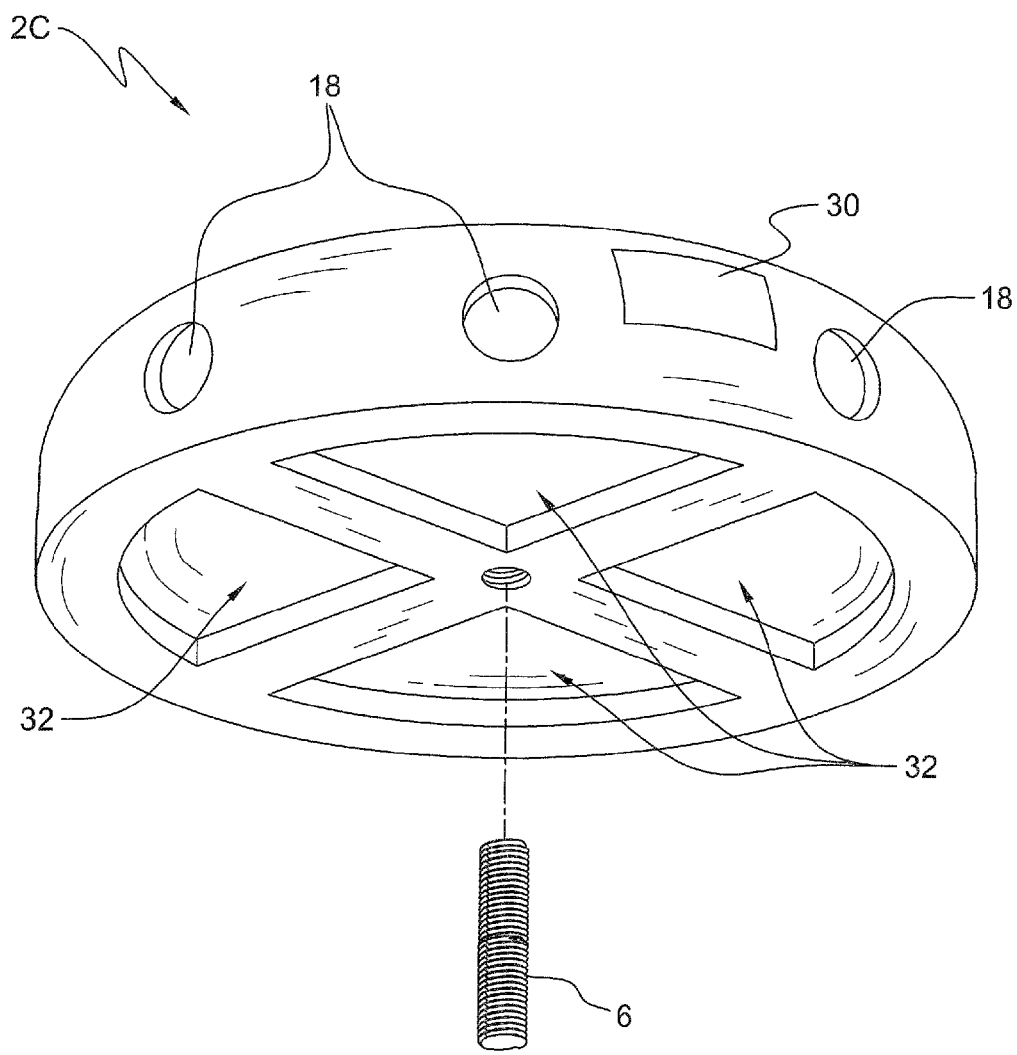
FIG. 5 depicts a side view of a one-piece upper housing 2A.

Alternatively, the upper receptacle may comprise an upper housing 2C that is a one single piece formed with an opening or closable window or doorway 30 through which deodorizer or repellent is loaded into the cavity for delivery to the internal volume of a container over time, as shown in FIG. 5. In upper housing 2C, there are no separate upper 3*a* and lower 3*b* sections (FIG. 3A) or multiple sections 3*c*, 3*d*, 3*e* (FIGS. 3B, 3C).

Figure 4:
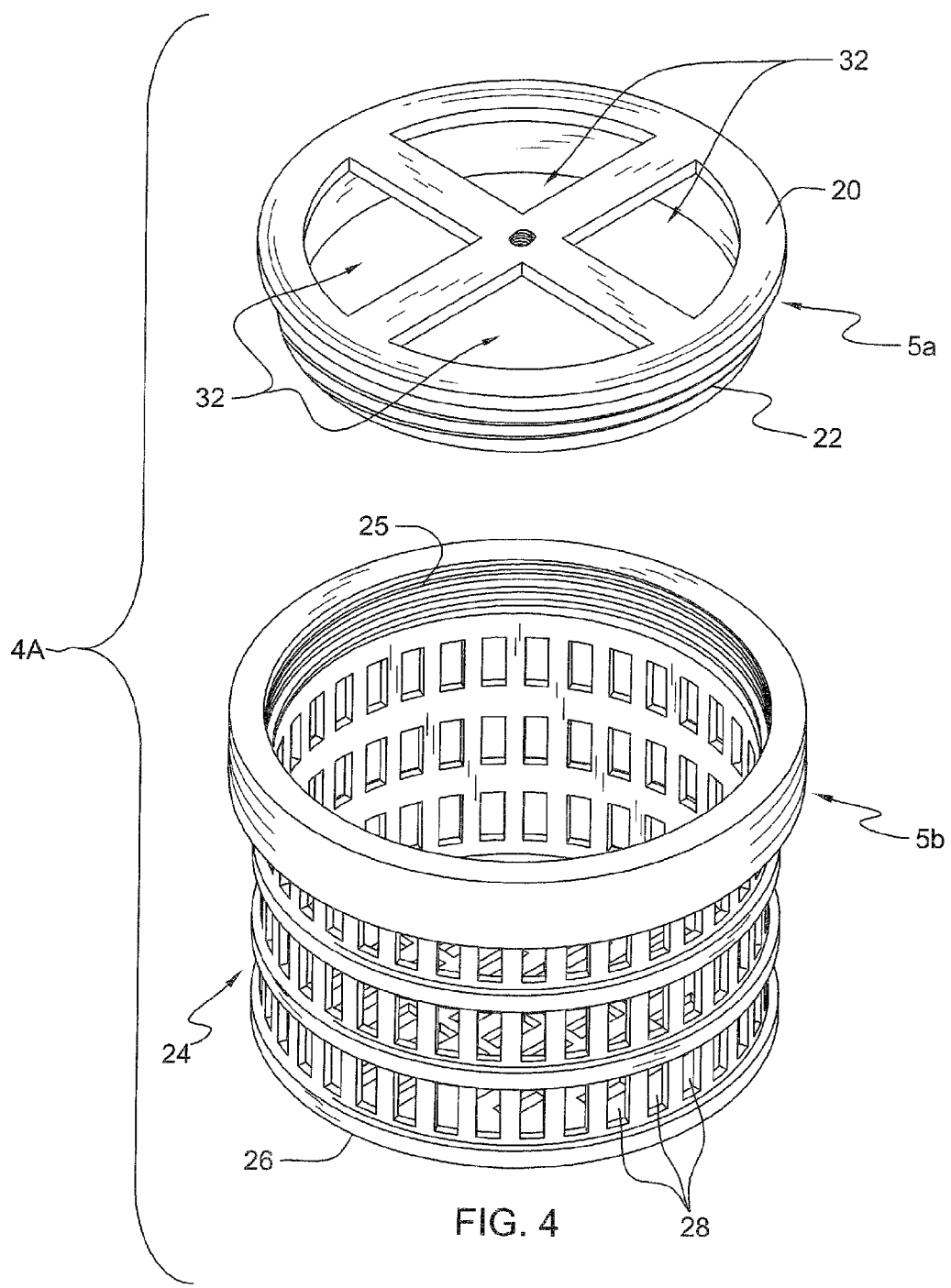
FIG. 4 presents an exploded side perspective view of a lower housing 4A for use in the system.

The lower housing 4A, which is normally contained within the inner volume of the container (not shown) when the system is attached to lid or cover 8, is comprised of respective upper 5*a* and lower sections 5*b*. Lower housing 4A may be constructed like upper housing 2A, as shown in FIG. 4. That is, lower housing 4A may comprise an upper section 5*a* formed with a substantially flat disk-like member 20. Disk-like member 20 is configured with a threaded side 22. A lower section 5*b* of lower housing 4A comprises a substantially cylindrical portion 24 extending up from a substantially flat base 26 to form a receptacle with an inner volume or cavity. An upper inner surface of the substantially cylindrical portion 24, opposite that portion to which the substantially flat base 26, is formed with a threaded portion 25 that complements the threaded side 22 of the disc-like member. Substantially flat base 26 screws into, and is released from the upper inner surface of the substantially cylindrical portion 24 thereby.

Please note that while the deodorizer and the repellent are preferably in solid form, same also may comprise a liquid form. Where the deodorizer and the repellent is in a form of a liquid, it must be contained in a delivery device suitable for positioning in the receptacle housing in such a way that it can be maintained stably over time and delivered conventionally, as is the case in the solids.

Figure 6:
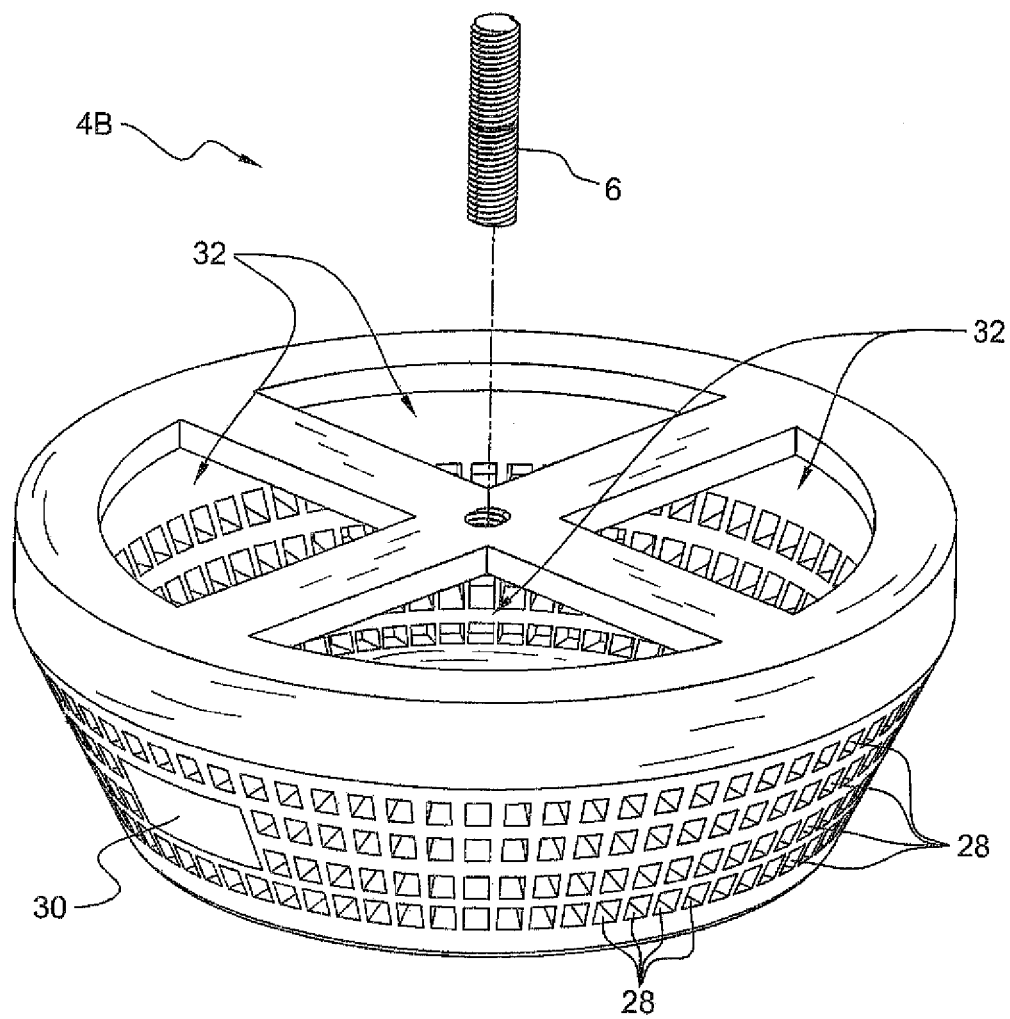
FIG. 6 depicts a side view of a one-piece lower housing 4B.

The lower section 5*b* (of lower housing 4A) includes a plurality of openings 28 in the cylindrical surface 24. Preferably, openings 28 also are included in the substantially flat base 26. The openings 28 communicate deodorizer placed in the cavity of lower housing 4A to the environment (in the container volume). Alternatively, the lower receptacle may comprise a lower housing 4B formed as a single-piece receptacle, as shown in FIG. 6. Lower housing 4B includes an opening or closable window or doorway 30 through which deodorizer or repellent is loaded into the inner cavity or volume. Of course the repellent or deodorizer is delivered through holes 28 to the internal volume of a container over time.

The connector 6 connects the upper (2A, 2B, 2C) and lower housings (4A, 4B). Preferably, the connector 6 at one end attaches to or is integral with the substantially flat disc-like member 20 comprising the upper section 5*a* of the lower housing (4A, 4B). At its other end, the connector 6 attaches to or is integral with the substantially flat base 16 of the lower section 3*b* of the upper housing (2A, 2B, 2C). The connector 6 extends through an opening in the container cover 8, as shown.

Alternatively, the connector 6 may be first passed through an opening in the cover 8, and permanently affixed to the cover. Thereafter, each of the substantially flat disc-like member 20 of the upper section 5*a* of the lower housing (4A, 4B) and the substantially flat base 16 of the lower section 3*b* of the upper housing (2A, 2B, 2C) are detachably connected to the cover 6 via each respective end of the connector 6.

The connector 6 preferably comprises a screw-like member extending from either of the substantially flat base 16 and the substantially flat disc-like member 20, that is turned to extend into a complementary machined bores in the opposing surface (substantially flat disc-like member 20 of the lower housing 4A, 4B and substantially flat base 26 of the upper housing 2A, 2B, 2C), coupling the upper 2A, 2B, 2C and lower 4A, 4B housings together.

Figure 7:
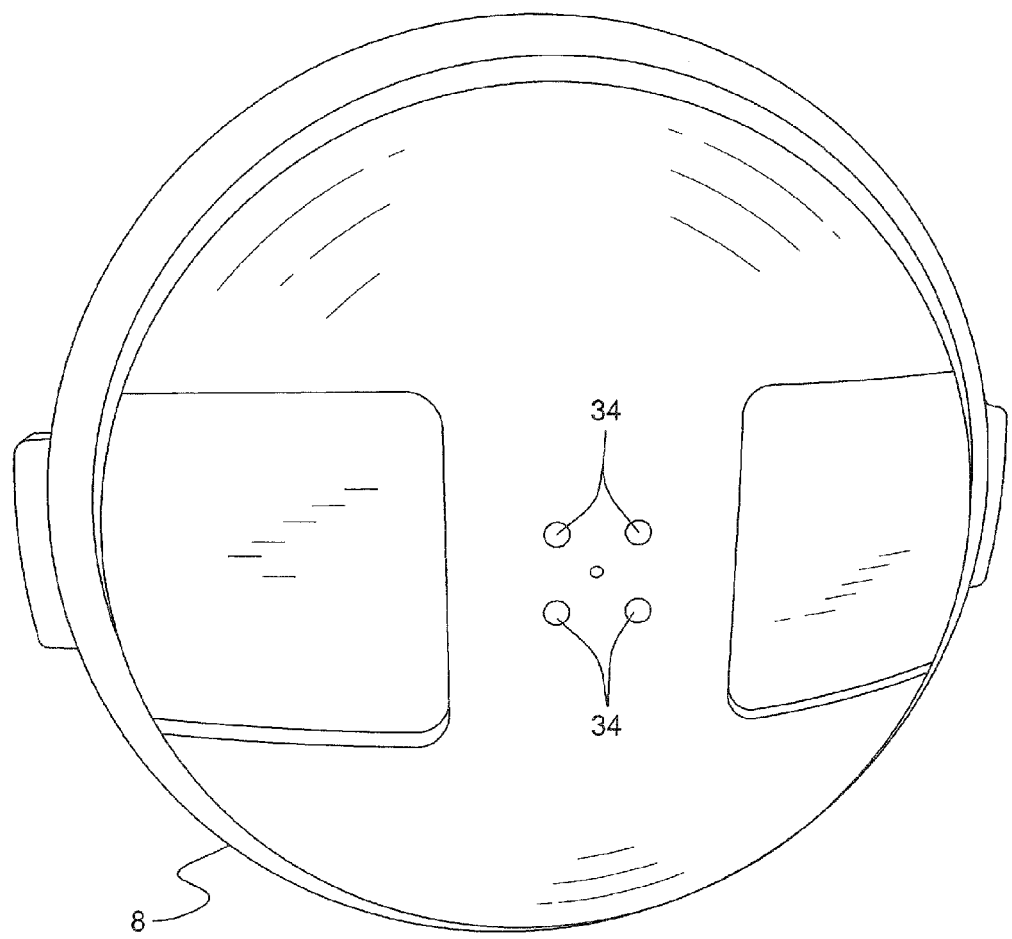
FIG. 7 depicts a view looking down on a container cover 8.

In an alternative embodiment, there are interconnecting holes 32 in the substantially flat base 16 of the upper housing 2A, 2B, 2C that align with interconnecting holes 32 in the substantially flat disk-like member 20 of the lower housing 4A, 4B that facilitate fluid communication between the inner volumes of the respective upper and lower housings. Please note that such embodiment requires that the cover 8 include cover holes for interconnecting 34, as shown in FIG. 7, which must align with the interconnecting holes 32. When aligned, an active deodorizer or repellent may be placed in either or both receptacles. Please further note, however, that accommodating such through-communication requires that the container cover 8 is processed to punch through holes and that the through holes in the cover 8, in the substantially flat base 16 of the upper housing 2A, 2B, 2C and in the substantially flat disc-like member 20 of the lower housing 4A, 4B must be aligned.

The following list of reference signs of various elements mentioned above is included (as follows), for ease of explanation:

LIST OF REFERENCE CHARACTERS 2A upper cylindrical housing forming receptacle
2B alternative upper cylindrical housing forming receptacle
2C alternative upper cylindrical housing forming receptacle
3*a* upper section of upper cylindrical housing 2A
3*b* lower section of upper cylindrical housing 2A
3*c* upper cover of upper section of upper cylindrical housing 2B
3*d* lower cover of upper section of upper cylindrical housing 2B
3*e* lower section of upper cylindrical housing 2B
4A lower cylindrical housing forming receptacle
4B alternative lower cylindrical housing forming receptacle
5*a* upper section of lower cylindrical housing 4A
5*b* lower section of lower cylindrical housing 4A
6 connector
7*a* handle part for upper cover of upper section of upper cylindrical housing 2B
7*b* inner detent element that is inserted into handle part 7*a* and allows for radial movement of upper cover about lower cover when handle 7 is grasped and turned/spun radially
8 lid or cover
9 radially extending slots in upper cover of upper section of upper cylindrical housing 2B
10 substantially arcuate part of upper section(s)
11 flange-like portion that depends from substantially arcuate part 10
12 substantially cylindrical portion of upper section(s)

14 substantially cylindrical portion of lower section(s)
16 substantially flat base or surface of lower section(s)
18 through holes
20 substantially flat disc-like member of upper section 5a of lower housing(s)
22 threaded side
24 substantially cylindrical portion of lower section
25 threaded inner surface of substantially cylindrical portion
26 substantially flat base
28 openings
30 openable and closable window or doorway
32 interconnecting holes
34 cover holes for intercommunicating In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

What is claimed is:

1. A system for delivering deodorizer and a repellent for use with a container, comprising:
   a first receptacle comprising a first housing shell surrounding a first inner volume for holding at least one of a repellent and a deodorizer, the first housing shell including an opening enabling fluid communication with the first inner volume;
   a second receptacle comprising a second housing shell surrounding a second inner volume for holding at least one of a repellent and a deodorizer, the second housing shell including an opening enabling fluid communication with the first inner volume; and
   a connector for detachably connecting the first receptacle to the second receptacle;
   wherein during intended use, an end of the connector is passed through a through-hole in a container cover having substantially planar upper and lower surfaces in order to interconnect the first receptacle to the second receptacle such that the first receptacle is positioned upon and above the upper surface of the container cover and the second receptacle is positioned upon and below the lower surface of the cover.

2. The system as set forth in claim 1, wherein the connector is permanently attached to the first receptacle.

3. The system as set forth in claim 1, wherein during intended use, the first receptacle holds a repellent and the second receptacle holds a deodorizer.

4. The system as set forth in claim 1, wherein first receptacle comprises an upper section and a lower section, wherein the upper section comprises a substantially flat upper part or top from which depends or extends a flange-like cylindrical portion, and wherein the lower section comprises a substantially cylindrical portion with a substantially flat base or surface and wherein the upper and lower sections are detachably connected.

5. The system as set forth in claim 4, wherein the lower section is open at its end opposite the flat base, wherein the flange-like cylindrical portion of the upper section is open at its end opposite the substantially flat upper part and wherein a diameter of the substantially flat base or surface is slightly less than a diameter of the substantially flat upper part allowing for the lower section to slide into the upper section and form the first receptacle.

6. The system as set forth in claim 4, wherein the opening includes a plurality of through-holes in both the flange-like cylindrical portion and the substantially cylindrical portion that are aligned in varying degree and affect an amount or size of the through-hole openings.

7. The system as set forth in claim 1, wherein the second receptacle comprises an upper section formed with a substantially flat disk-like member and a lower section comprising a substantially cylindrical portion extending up from a substantially flat base to form an inner volume of the second receptacle.

8. The system as set forth in claim 7, wherein the substantially flat disk-like member configured with a threaded side and wherein an upper inner surface of the substantially cylindrical portion is formed with a threaded portion that complements the threaded side of the disc-like member, allowing the flat disk-like member to be turned into and fastened to the substantially cylindrical portion.

9. The system as set forth in claim 8, wherein the opening comprises a plurality of through-holes or openings in the substantially cylindrical portion.

10. The system as set forth in claim 9, wherein the opening further comprises a plurality of through-holes or openings in the substantially flat base.

11. The system as set forth in claim 1, wherein first and second receptacles comprise substantially cylindrical housings formed as one piece and wherein the openings in the respective first and second receptacles are formed by a plurality of through-holes for dispensing the deodorizer and/or repellent and at least one opening or closable window for placement of the deodorizer and/or repellent therein.

12. The system as set forth in claim 1, wherein the first and second receptacles are formed of any of the group consisting of: plastic, polyvinyl, high density polyethylene (HDPE), polypropylene, hardened rubber, metal, recycled materials and a combination of these materials.

13. The system as set forth in claim 1, wherein the repellent is one of the group including insect repellent, rodent repellent, raccoon repellent, bear repellent and wherein the deodorizer is one the group consisting of carbon chips, carbon granules, carbon sticks, mesh bags comprising carbon, activated carbon, materials that emit botanical fragrances, citrus fragrances, woodsy fragrances, floral fragrances, fruity fragrances.

14. A container that delivers a deodorizer to a container inner volume and a repellent to an area proximate but external to the container, the container comprising:
   a container part formed as a hollow cylinder having a flat base at one end, an opening at its other end and cylindrical volume therebetween;
   a container cover formed to cover the opening in the container part that includes a centrally-located through hole;
   a first receptacle comprising a first housing shell surrounding a first inner volume for holding the repellent and including an opening facilitating fluid communication of the repellent from the first inner volume;
   a second receptacle comprising a second housing shell surrounding a second inner volume for holding the deodorizer and including an opening facilitating fluid communication from the first inner volume; and
   a connector for detachably connecting the first receptacle and the second receptacle to the container cover via the centrally located through hole.

15. The container as set forth in claim 14, wherein the connector extends through the opening in the container cover and fixes the first receptacle upon an upper surface of the container cover and fixes the second receptacle upon a lower surface of the container cover and wherein a dimension of the openings is adjustable to control a rate of fluid communication from the first and second receptacles.

16. The container as set forth in claim 15, wherein the cover includes further openings that allow for fluid communication between the first and second receptacles therethrough.

17. A system for delivering deodorizer and/or repellent for use in a container, comprising any of a group consisting of a first receptacle, a second receptacle and both and a connector for detachably connecting the first receptacle, the second receptacle or both to a container cover;

wherein the first and second receptacles comprise respective first and second housing shells surrounding corresponding first and second inner volumes for holding at least one of a repellent and a deodorizer, wherein the first and second housing shells include one or more openings enabling placement of the deodorizer and/or repellent in the receptacles and fluid communication with the inner volumes and the connector passes through a surface of the container cover to connected the first receptacle positioned on an upper surface of the container cover to the second receptacle positioned on a lower surface of the container cover.

\* \* \* \* \*